United States Patent [19]
Cope et al.

[11] Patent Number: 5,776,079
[45] Date of Patent: Jul. 7, 1998

[54] RETROGRADE-ANTEGRADE CATHETERIZATION GUIDE WIRE

[75] Inventors: Constantin Cope, Elkins Park, Pa.; Mark A. Griffin, Bloomington, Ind.

[73] Assignee: Cook Incorporated, Bloomington, Ind.

[21] Appl. No.: 692,568

[22] Filed: Aug. 6, 1996

[51] Int. Cl.$^6$ ............................................. A61M 25/01
[52] U.S. Cl. .................................................. 600/585
[58] Field of Search ............................... 128/657, 772; 604/280; 607/119, 122, 118, 132; 600/434, 585

[56] References Cited

U.S. PATENT DOCUMENTS

| | | | |
|---|---|---|---|
| 4,245,624 | 1/1981 | Komiya | 128/772 |
| 4,808,164 | 2/1989 | Hess | 128/657 |
| 5,030,204 | 7/1991 | Badger et al. | |
| 5,054,501 | 10/1991 | Chuttani et al. | |
| 5,304,131 | 4/1994 | Paskar | |
| 5,315,996 | 5/1994 | Lundquist | 607/119 |
| 5,482,037 | 1/1996 | Borghi | 128/657 |

FOREIGN PATENT DOCUMENTS

| | | |
|---|---|---|
| 0436303 | 7/1991 | European Pat. Off. |
| 0468645 | 1/1992 | European Pat. Off. |

Primary Examiner—William E. Kamm
Assistant Examiner—George R. Evanisko
Attorney, Agent, or Firm—Richard J. Godlewski

[57] ABSTRACT

An catheterization apparatus 10 for reversing the retrograde or antegrade direction of catheterization includes a guide wire 12 foldable upon itself for partial introduction into a vessel 68 of a patient. The guide wire 12 first includes a resilient, elongated member 14 having a curved end 16 and a remainder 17 having a second, bent end 18. The guide wire 12 also includes a flexible tether 22 connected to the tip 20 of the curved end 16 of the elongated member 14. The elongated member 14 is preferably formed from a wire core or mandrel 24 covered by a continuous coiled wire 30. The catheterization apparatus 10 preferably further includes a catheter through which the guide wire 12 is introduced into the vessel 68. The catheter can be of conventional construction and operability. Preferably, however, the catheter is a highly flexible and relatively short intermediary catheter 56, employed only temporarily during use of the retrograde-antegrade guide wire 12. The catheterization apparatus 10 can also include an inserter sheath 60 engageable with the catheter 56 to facilitate passage of the guide wire 12 through the catheter 56. The apparatus 10 is particularly advantageous in that its use avoids the need to establish a second access site. Moreover, the apparatus 10 is relatively simple and reliable in construction and use, and is relatively low in cost, at least in comparison to the costs and risks of the establishment of a second access site. The apparatus 10 is atraumatic during use, that is, it does not significantly damage the blood vessel or other vessel during reversal of the direction of catheterization. The apparatus 10 is useful in vessels of both large and small diameter, and facilitates the selective engagement of a catheter with a bifurcation branch in a vessel.

15 Claims, 4 Drawing Sheets

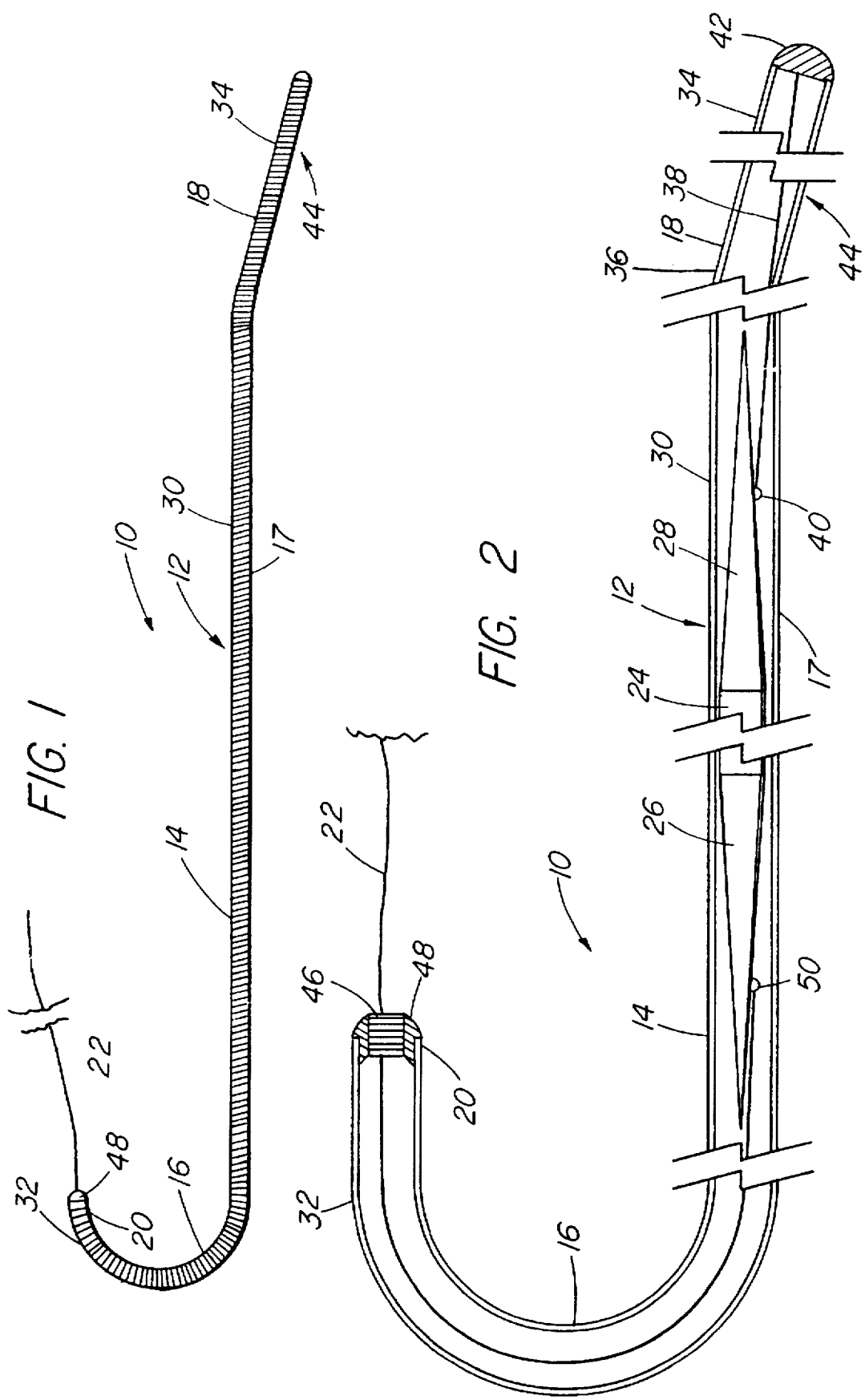

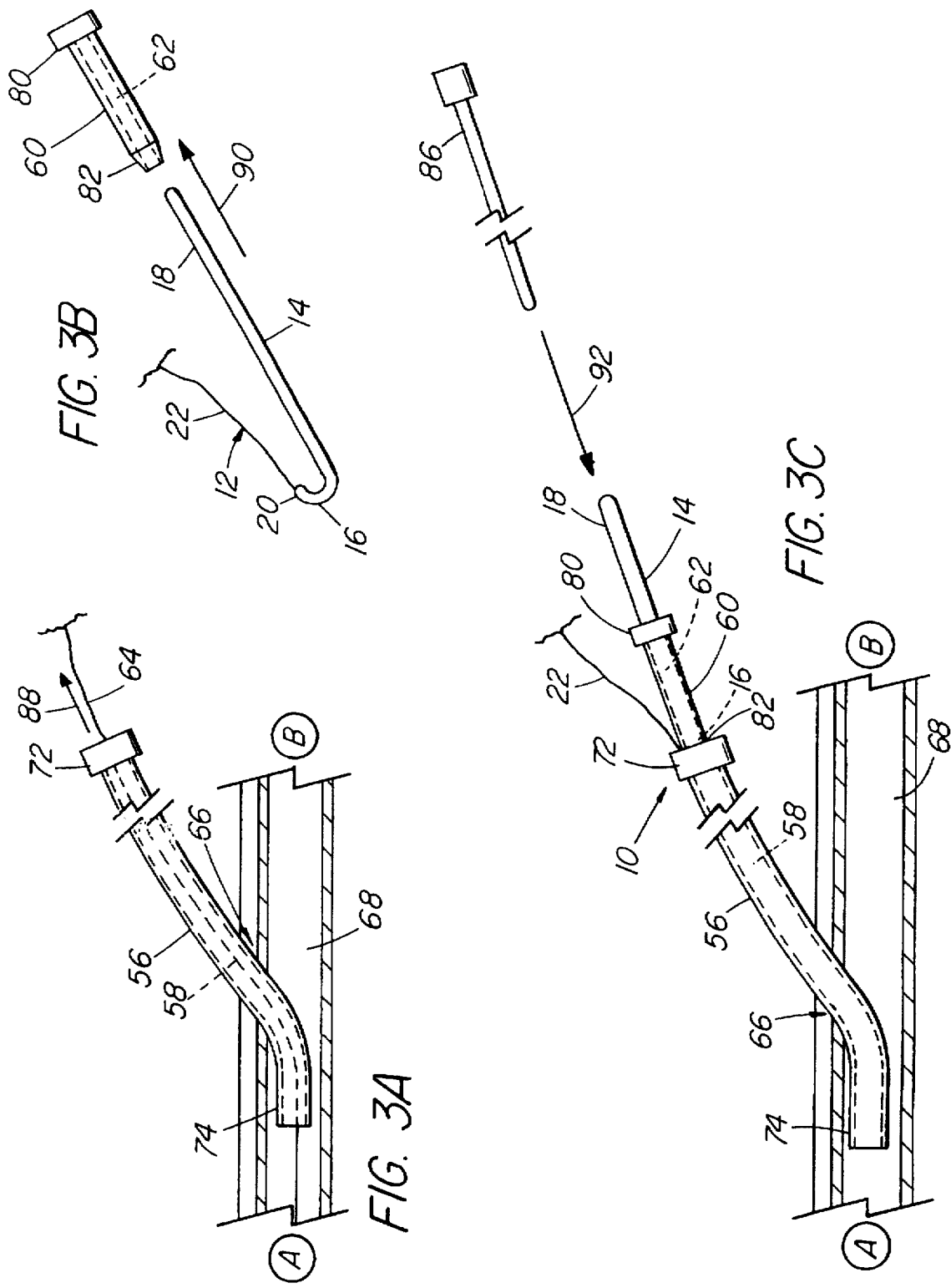

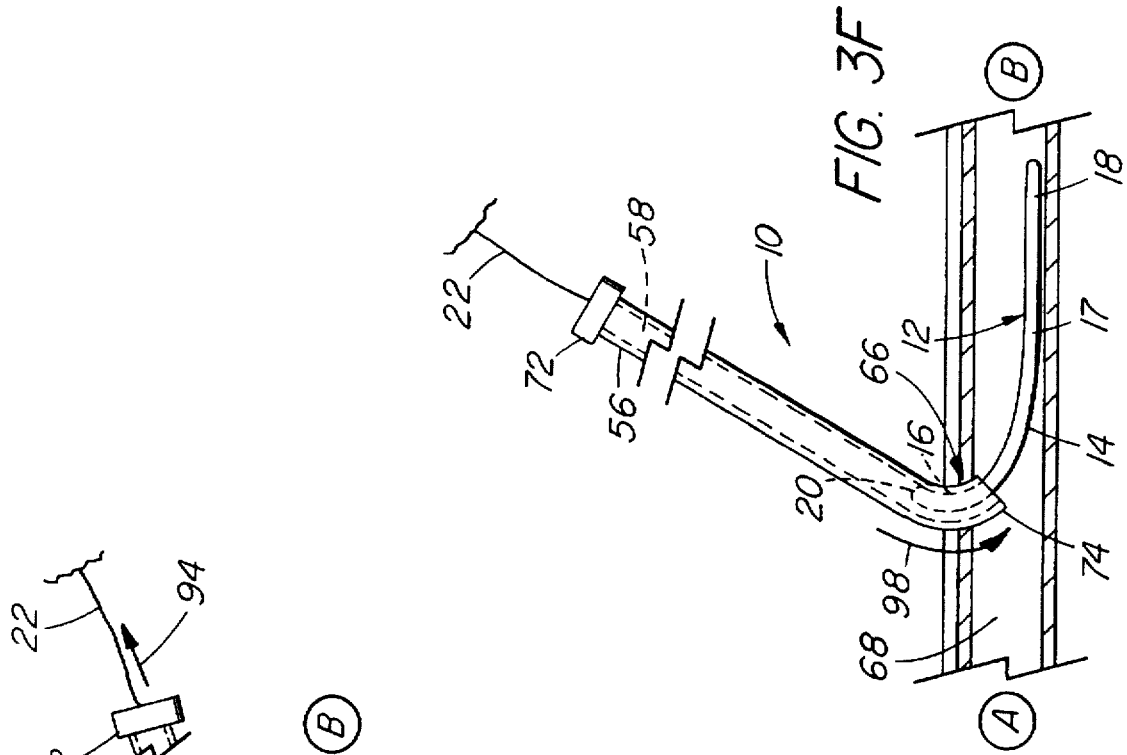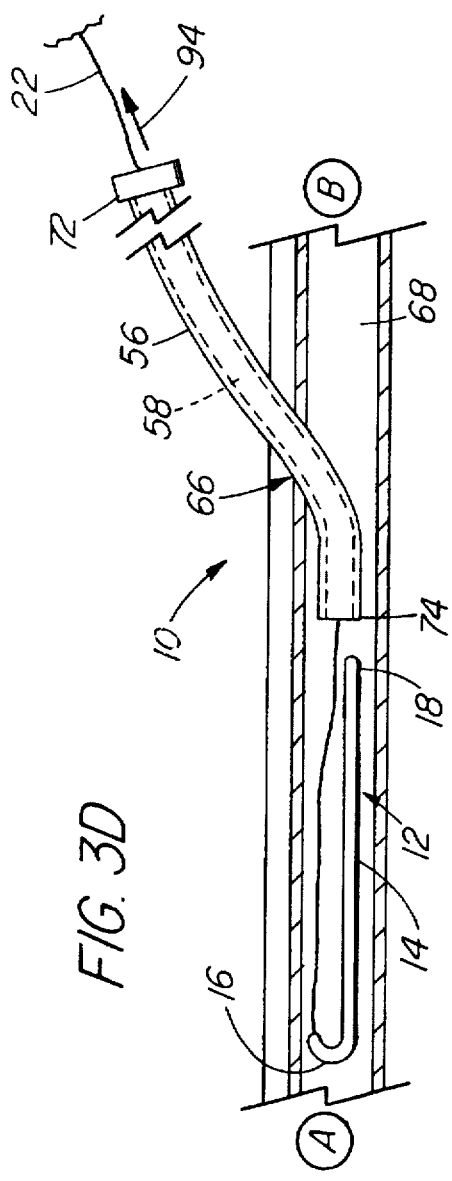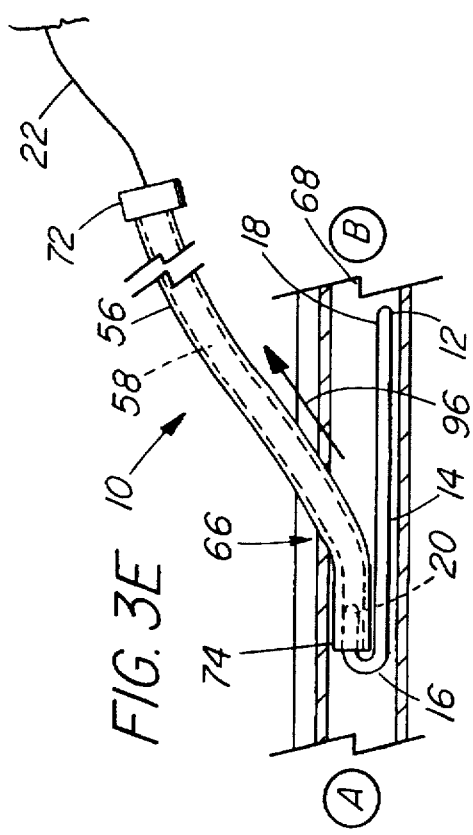

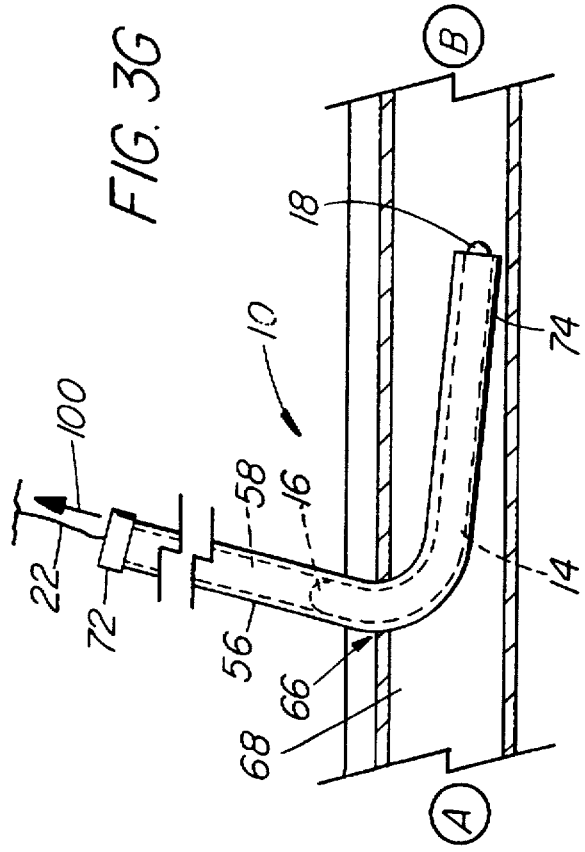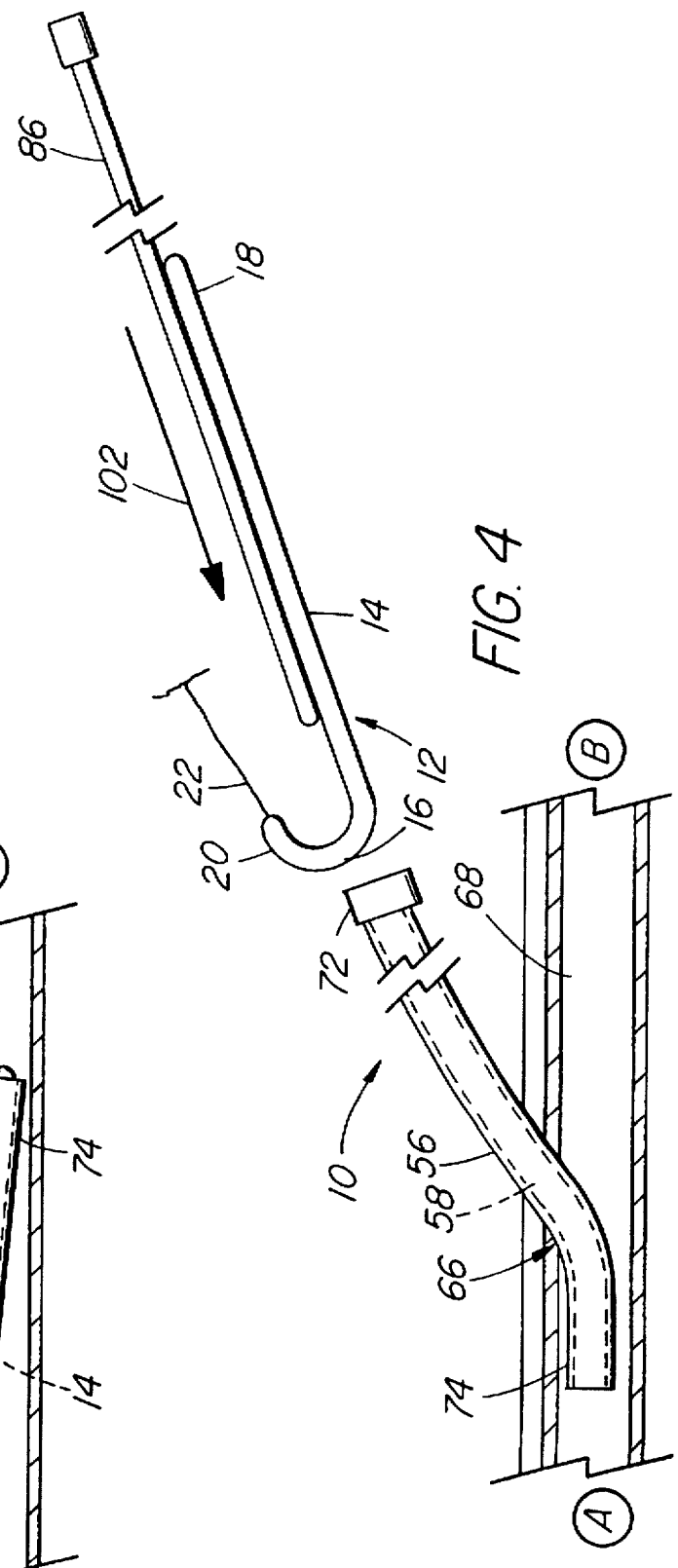

RETROGRADE-ANTEGRADE CATHETERIZATION GUIDE WIRE

TECHNICAL FIELD

This invention relates generally to medical procedures, and more particularly to procedures for accessing the vascular system or other system of tubular structures in a patient.

BACKGROUND OF THE INVENTION

Numerous medical procedures involve the introduction of a catheter or the like into a vessel or other tubular structure in the body. Vessels and other tubular structures which can be accessed by catheterization include the blood vessels, the bowel and digestive tract, the bile ducts, the ureters and urinary tract, and several others. Known catheterization procedures include the positioning and inflation of nondistending balloons for opening a constricted vessel, the positioning and expansion of stents for maintaining an open lumen in a constricted vessel, the intravenous administration of nutrient fluids, the delivery of whole blood or blood products, the sampling of blood and the administration of chemotherapeutic agents or other drugs.

The first step in the performance of these procedures is the establishment of a site through the skin by which access is had to the vessel or other tubular structure. A guide wire is introduced into the vessel or other structure, and the catheter advanced in the vessel or structure in one direction or another to a desired location. If this direction is opposite to the direction of fluid flow in the vessel or other structure, it is referred to as the "retrograde" direction. On the other hand, if this direction is the same as the direction of fluid flow in the vessel, it is referred to as the "antegrade" direction. By way of example, catheterization of the femoral artery, axillary artery or brachial artery for access to the vessels of the abdomen or thorax is carried out by advancement of the catheter in the retrograde direction.

It is sometimes the case that more than one catheterization procedure needs to be performed. More particularly, after the establishment of an access site, for example, for the introduction of a catheter in the retrograde direction, it may be discovered that it is necessary or desirable to reintroduce the catheter in the antegrade direction. Alternatively, it may be necessary or desirable to introduce a second, different catheter into the vessel or other structure in the antegrade direction. Such a situation may arise, for example, when lesions requiring balloon angioplasty are found in a direction opposite to the access site.

It has generally been found to be very difficult, sometimes even impossible, to reverse the direction of catheter advancement through the initial access site. A new access site in the opposite direction (such as the antegrade direction) must normally be established in order to permit the advancement of a catheter in that opposite direction, for example, for PTA ballooning or thrombolysis.

The need to prepare a new access site is undesirable for several reasons. The time needed for preparation of the new access site delays the performance of the catheterization procedure on the patient. The new access site must be prepared by trained medical personnel, adding to the cost of patient treatment. The unnecessary establishment of access sites increases patient discomfort and increases the risk of patient infection.

Perhaps most importantly, however, the repeated perforation of a blood vessel or other body vessel can result in damage or even collapse of the vessel.

Some techniques are known for achieving catheterization in a direction opposite to an established direction of catheterization. Each, however, is subject to its own drawbacks. The insertion of a second catheter from either the contralateral or ipsilateral side is undesirable for the reasons mentioned above. Catheterization with a sidewinder-type catheter is only rarely performed because the catheter can cause a high degree of trauma in vessels of small or medium diameter. For this reason, the use of a sidewinder-type catheter is typically limited to its introduction into the aorta and its advancement down the superficial femoral artery. A final technique involves the use of a "hockey stick" catheter having a small, right angle tip allowing 180 degree rotation of the catheter direction. Unfortunately, such a catheter is only useful in vessels of large diameter. Moreover, such a catheter is easily subject to accidental extraction during use.

It should thus be clear that it would be highly desirable to have an apparatus for reversing the direction of catheterization within a patient, either retrograde to antegrade, or antegrade to retrograde, which does not entail the establishment of a second access site. It would also be highly desirable to have such an apparatus that is relatively simple and reliable in construction and use, and which is relatively low in cost, at least in comparison to the costs and risks incurred in establishing a second access site. It would further be desirable to have such an apparatus that is atraumatic during use, that is, an apparatus which does not significantly damage the blood vessel or other vessel during reversal of the direction of catheterization. Finally, it would be desirable to have such an apparatus that is useful in vessels of both large and small diameter, and which facilitates the selective engagement of a catheter with a bifurcation branch in a vessel.

SUMMARY OF THE INVENTION

The foregoing problems are solved and a technical advance is achieved in an illustrative catheterization apparatus including a retrograde-antegrade guide wire. Applicant has discovered a guide wire having portions of differing flexibility which allows a catheter to be selectively advanced in either the antegrade or the retrograde direction from a single access site. The retrograde-antegrade guide wire can be used with one or more catheters of conventional construction and conventional operation. However, the retrograde-antegrade guide wire of the present invention is most preferably used in conjunction with a relatively short and very flexible intermediary catheter. This intermediary catheter serves as a temporary replacement for the functional catheter or catheters. The catheterization apparatus of the present invention can comprise the combination of the retrograde-antegrade guide wire and this intermediary catheter, or any conventional catheter.

More particularly, Applicant's guide wire comprises an elongated member having a flexible, limp tether connected to it. The elongated member is resilient and flexible, but is somewhat less flexible than the tether. The elongated member is generally "J"-shaped and has a flexible, curved end to whose tip the tether is connected. In use, the entirety of the elongated member is introduced through a catheter (preferably, the intermediary catheter mentioned above) and into the vessel in a first direction, either antegrade or retrograde, with the curved portion leading the remainder of the member through the access site, and the tether extending outside the patient.

The tether is then partially withdrawn until the curved portion of the elongated member is level with the access site and the curved end of the elongated member is received in the distal tip of the catheter. The remainder of the elongated member is still positioned in the vessel, however, extending in a second direction opposite the first direction. The catheter is then advanced along the tether and the elongated member, and advanced in the vessel in the second direction.

The retrograde-antegrade guide wire employed in the catheterization apparatus and method of the present invention can be positioned in the vessel in any of several ways. The guide wire can be introduced through a single or plural lumen operative catheter which initially extends in the first direction but is ultimately desired to be advanced in the second direction. The guide wire can instead be introduced through an intermediary catheter. A conventional guide wire can be fed through the intermediary catheter once its direction has been reversed, the intermediary catheter removed from the conventional guide wire, and an operative catheter then advanced in the second direction over the conventional guide wire.

In a first aspect, then, the present invention is directed to a catheterization apparatus which first comprises a retrograde-antegrade guide wire foldable upon itself for partial introduction into a vessel or other tubular structure in a patient. The guide wire comprises a resilient, elongated member having a flexible, curved end, and a remainder having a second end opposite the curved end. The curved end of the elongated member has a tip to which a limp, flexible tether is connected. The curved end is preferably more flexible than the remainder of the elongated member. The second end of the elongated member is preferably bent at an angle of about 10 to 15 degrees.

The elongated member conveniently comprises a wire core including first and second tapered ends, and a continuous coiled wire positioned over the wire core. The coiled wire preferably includes a portion extending beyond the second end of the wire core, and the guide wire can further comprise a safety wire connecting the second end of the wire core to the coiled wire portion. An atraumatic tip is thereby formed on the second end of the elongated member. The continuous coiled wire preferably has a first end adjacent to the tether, and the guide wire can include a short coiled wire segment attached to and received in the first end of the continuous coiled wire, connecting the tether to the coiled wire.

In this first aspect, the catheterization apparatus of the present invention also preferably comprises the relatively short, highly flexible intermediary catheter for introducing the elongated member of the retrograde-antegrade guide wire into the vessel or other tubular structure, as well as an inserter sheath to facilitate the insertion of the guide wire into the intermediary catheter.

In a second aspect, the present invention is directed to a retrograde-antegrade guide wire which comprises a specific combination of the preferred elements described above.

In a final aspect, the present invention is directed to a method of changing the retrograde-antegrade direction of catheterization entailing the use of the catheterization apparatus described above, including the disclosed retrograde-antegrade guide wire. The method broadly comprises the steps of (a) introducing the elongated member of the retrograde-antegrade guide wire into the vessel or other tubular structure in a first direction, with the second end of the elongated member extending in a second direction; and (b) advancing the catheter over the elongated member in the second direction.

The catheterization apparatus of the present invention is particularly advantageous in that its use avoids the need to establish a second access site. Moreover, the apparatus is relatively simple and reliable in construction and use, and is relatively low in cost, at least in comparison to the costs and risks establishing a second access site. The apparatus is atraumatic during use, that is, it does not significantly damage the blood vessel or other vessel during reversal of the direction of catheterization. The apparatus is useful in vessels of both large and small diameter, and facilitates the selective engagement of a catheter with a bifurcation branch in a vessel.

BRIEF DESCRIPTION OF THE DRAWING

A better understanding of the present invention will now be had upon reference to the following detailed description, when read in conjunction with the accompanying drawing, wherein like reference characters refer to like parts throughout the several views, and in which:

FIG. 1 is a perspective view of the preferred embodiment of the present invention;

FIG. 2 is a longitudinal cross-sectional view of the preferred embodiment of the present invention;

FIGS. 3A through 3G are partial cross-sectional views of the preferred method of use of the preferred embodiment of the present invention; and FIG. 4 is a partial cross-sectional view of another method of use of the preferred embodiment of the present invention.

DETAILED DESCRIPTION

With reference first to FIG. 1, a retrograde-antegrade guide wire 12 comprised within a catheterization apparatus 10 according to the present invention is thereshown and first comprises a resilient, elongated member 14 having a flexible, curved end 16. Preferably, the curved end 16 of the elongated member 14 is more flexible than the remainder 17 of the elongated member 14. The remainder 17 of the elongated member also has a second end 18 opposite the curved end 16, bent at an angle of about 10 to 15 degrees. This has two functions; it makes it easier for the elongated member 14 to pass around a catheter tip during its manipulation in a vessel or other tubular structure in the body, and it allows the selection of which part of a bifurcated vessel or other tubular structure the elongated member will enter during its use.

In general terms, the elongated member 14 is essentially "J"-shaped, with the straight part of the "J" being several times longer (preferably, about on the order of ten times longer) than the width of the "hook" of the "J". Conveniently, the curved end 16 of the elongated member 14 has a width of about 2 to 3 mm, and the remainder 17 of the elongated member 14 is about 10 or 11 cm long.

The curved end 16 of the elongated member 14 has a tip 20 opposite the remainder 17 of the elongated member 14. The retrograde-antegrade guide wire 12 further comprises a limp, flexible tether 22 connected to the tip 20 of the curved end 16. The tether 22 is conveniently formed from about a 40 cm segment of 0.007 inch diameter, flexible, stranded stainless steel wire. Alternatively, a braided material such as a braided plastic suture material can also be used.

With continued reference to FIG. 1, but with additional reference to FIG. 2, the elongated member 14 includes a wire core 24 (sometimes referred to as a mandrel). The wire core 24 is conveniently formed from about 5 to 7.5 cm of 0.017 inch diameter stainless steel or nitinol wire. The wire core 24 preferably has a first tapered end 26 and a second tapered end 28.

The elongated member 14 also includes a continuous coiled wire 30 positioned over the wire core 24. The continuous coiled wire 30 has a first end 32 adjacent to the tether 22 and a second end 34 opposite the first end 32. The coiled wire 30 is conveniently formed from about 13 cm of 0.032 inch diameter stainless steel wire.

The coiled wire 30 preferably includes a portion 36 at the second end 34 extending beyond the second end 28 of the wire core 24. A safety wire 38 connects the second end 28 of the wire core 24 and the extending portion 36 of the coiled wire 30. The safety wire 38 is affixed to the second end 28 of the wire core 24 in any convenient manner, for example, by a bead 40 of solder. The safety wire is affixed to the second end 34 of the coiled wire 30, more particularly to the extending portion 36 of the coiled wire 30, in any convenient manner, for example, by a weld 42.

The safety wire 38, the extending wire portion 36, the weld 42 and bead 40 of solder thus together form an atraumatic tip 44 on the second end 18 of the elongated member 14 of the retrograde-antegrade guide wire 12. The atraumatic tip 44 of the guide wire 12 could of course be formed in any of a variety of other ways.

The tether 22 can be connected to the elongated member 14 in any of several ways. Preferably, the tether 22 is first affixed to the first tapered end 26 of the wire core 24 by a bead 50 of solder. The tether 22 is then affixed to the tip 20 of the curved end 16 of the elongated member 14 by passing it through a short segment 46 of coiled wire received in the first end 32 of the continuous coiled wire 30. The short segment 46 is about 2 mm long and formed of 0.018 inch diameter stainless steel wire. A shoulder 48 of solder affixes the short coil segment 46, the tether 22 and the first end 32 of the coiled wire 30 to one another.

The method of using the apparatus 10 of the present invention for reversing the retrograde-antegrade direction of advancement of a catheter can now be readily understood. The retrograde-antegrade guide wire 12 can be used directly to reverse the direction of advancement of a conventional, operable, single or plural lumen catheter. However, as shown in FIGS. 3A through 3G, the method of the present invention is typically more advantageously carried out with a catheterization apparatus 10 which, in addition to the guide wire 12, further comprises a relatively short, highly flexible, intermediary catheter 56. The intermediary catheter 56 has a lumen 58 dimensioned to allow passage of the retrograde-antegrade guide wire 12 therethrough when the guide wire 12 is folded upon itself, with the tether 22 lying generally parallel to the remainder 17 of the elongated member 14.

For use in conjunction with the specific embodiment of the retrograde-antegrade guide wire 12 disclosed above, the intermediary catheter 56 is conveniently 5.5 French in diameter and has an internal diameter at its distal tip 74 of 0.038 inches. The intermediary catheter 56 should be made of a soft, flexible plastic or synthetic material which can withstand a fairly acute turn without kinking. Soft, flexible polyethylene is particularly suited to this purpose.

The method of the present invention is even more advantageously carried out with a catheterization apparatus 10 which additionally comprises an inserter sheath 60 (FIGS. 3B and 3C) engageable with the intermediary catheter 56 so as to facilitate the introduction and passage of the guide wire 12 into and through the intermediary catheter 56. The inserter sheath 60 is generally rigid and has a lumen 62 dimensioned to receive the elongated member 14 of the guide wire 12 therein. Typically, the intermediary catheter 56 will be substantially shorter than a conventional catheter, and conveniently will be on the order of 15 to 20 cm long. Also typically, the inserter sheath 60 will only need to be on the order of half the length of the elongated member 14 of the guide wire 12, and conveniently can be no more than about 4 or 5 cm long.

Again, while the preferred method of use of the apparatus 10 of the present invention will first be described in conjunction with the intermediary catheter 56, it should be remembered that the method can also be carried out with a conventional, operable catheter whose tip is adequately flexible to allow it to be reoriented in the same manner as that of the intermediary catheter 56. Also, if the lumen of either the conventional catheter or the intermediary catheter 56 is wide enough, the method can also be carried out without the inserter sheath 60, and the retrograde-antegrade guide wire 12 introduced directly into the catheter lumen.

With respect to the particularly preferred method of the present invention, then, reference will be had to FIG. 3A, which shows the intermediary catheter 56 already positioned in a previously established access site 66 over a previously inserted conventional guide wire 64. The prior insertion of the conventional guide wire 64 in the vessel or other tubular structure 68 can be carried out in any suitable manner, well known to those skilled in this art.

The conventional guide wire 64 and the intermediary catheter 56 are shown in FIG. 3A extending in a first direction A in the vessel 68. The designation of this direction is arbitrary; the direction A can be either the retrograde direction or the antegrade direction, and the direction B is the opposite direction ultimately desired for catheterization. For example, initial diagnostic access to the abdominal and thoracic vasculature is typically had through an access site 66 in the groin of the patient, and retrograde catheterization performed through the femoral, axillary or brachial arteries. Lesions distal to the access site 66 would be treated by balloon angioplasty with a balloon catheter advanced in the antegrade direction from the access site 66. Other procedures may require that the initial catheterization be established in the antegrade direction.

It is highly preferred that the access site 66 be prepared in such a fashion so that the intermediary catheter 56 makes a fairly large angle through the access site 66 with respect to the vessel 68. More particularly, the angle at the access site should be between about 60 and about 75 degrees. This fairly large angle is the same throughout FIGS. 3A through 3G, FIG. 4, and FIGS. 5A and 5B. (Even though some of the Figures may show a shallower angle, this is merely an unintended result of the arrangement of the Figures on the sheets of drawings.) This fairly large angle should be maintained throughout the performance of the method of the present invention in order to reduce trauma to the access site 66 and vessel 68.

The intermediary catheter 56 is prepared for introduction of the retrograde-antegrade guide wire 12 by removing the conventional guide wire 64 through the lumen 58 of the catheter 56 in the direction of arrow 88. As shown in FIG. 3B, the guide wire 12 is prepared for such introduction by inserting the second end 18 of the elongated member 14 of the guide wire 12 through the distal end 82 of the inserter sheath 60, and passing the elongated member 14 through the lumen 62 of the inserter sheath 60 until the curved end 16 of the elongated member is fully received in the lumen 62 of the inserter sheath 60. The tether 22 is then positioned alongside the inserter sheath 60, so that the retrograde-antegrade guide wire 12 becomes folded over on itself. The distal end 82 of the inserter sheath 60 is then engaged with the proximal end 72 of the intermediary catheter 56 (FIG. 3C) so as to align the lumens 62 and 58 and allow movement of the elongated member 14 in the direction of arrow 92, and into the catheter 56. A conventional pusher 86 may be used to aid such movement once the second end 18 of the elongated member 14 lies within the inserter sheath 60 or within the intermediary catheter 56.

The retrograde-antegrade guide wire 12 is advanced through the intermediary catheter 56 until the position shown in FIG. 3D is achieved, in which the elongated member 14 of the guide wire 12 is entirely positioned in the vessel 68, but in which the tether 22 still extends partly outside the catheter 56. The tether 22 is then proximally withdrawn in the direction of arrow 94 until the tip 20 of the curved end 16 of the elongated member 14 is received in the distal tip 74 of the catheter 56. Some minor manipulation of the intermediary catheter 56 may be required to allow the second end 18 of the elongated member 14 to pass by the distal tip 74 of the catheter 56. However, since the second end 18 of the elongated member 14 is bent at an angle of about 10 to 15 degrees, such manipulation should be minimal or nonexistent.

The result of the partial withdrawal of the tether 22 is shown in FIG. 3E. The tether 22 and the intermediary catheter 56 are then distally withdrawn together in the direction of arrow 96, so as to bring the distal tip 74 of the catheter 56, as well as the tip 20 of the curved end 16 of the elongated member 14, level with the access site 66. During such withdrawal it is desirable to also withdraw the tether 22 slightly with respect to the intermediary catheter 56, so that the curved end 16 of the elongated member is drawn further into the lumen 58 of the catheter 56. As shown in FIG. 3F, this brings the remainder 17 of the elongated member 14 past the access site 66, extending in the second direction B.

The intermediary catheter 56 can now be advanced along the elongated member 14 in the direction of arrow 98, past the second end 18 of the elongated member in the second direction B (FIG. 3G). The retrograde-antegrade guide wire 12 can then be withdrawn from the catheter 56 in the direction of arrow 100, allowing reinsertion of the conventional guide wire 64 into the vessel 66 in the second direction B. The access site 66 is thereby made ready for subsequent catheterization in the second direction B; such subsequent catheterization can be carried out in any conventional fashion.

An alternative or additional procedure facilitated by the apparatus 10 of the present invention is the selective engagement of the intermediary catheter 56 and the guide wire 12 with a bifurcation branch of a vessel, for example, with the superficial femoral artery. The procedure would be identical to the method of use disclosed above, up to but not including the advancement of the intermediary catheter 56 over the second end 18 of the elongated member 14. Instead, the catheter 56 would be advanced only up to the second end 18, not over it. The catheter 56 and guide wire 12 would then be advanced together in the second direction B until the second end 18 of the elongated member 14 can be selectively slipped into the desired vessel branch. Because the second end 18 of the elongated member 14 is bent, such manipulation is relatively easy to perform, and can be monitored by fluoroscope. The intermediary catheter 56 can then be advanced over the second end 18 of the elongated member 14, the guide wire 12 removed from the catheter 56, and the conventional guide wire 64 reintroduced into the catheter 56. Subsequent catheterization can be carried out in any conventional manner.

It is highly desirable during the performance of any variation of the method of the present invention that the distal tip 74 of the intermediary catheter 56 (or distal tip of any other catheter employed) not be inadvertently withdrawn from the vessel 68 during the withdrawal of the tether 22 and catheter 56 shown in FIGS. 3E and 3F. First, if the intermediary catheter 56 exits the vessel 68 inadvertently, an undesirable degree of bleeding at the access site 66 may be encountered. More importantly, the great flexibility of the intermediary catheter 56 makes it difficult to reintroduce the catheter 56 through the access site 66 and into the vessel 68, even though the retrograde-antegrade guide wire 12 may maintain the patency of the access site 66 during such withdrawal. Reintroduction of the intermediary catheter 56 requires the application of a relatively great amount of pull to the tether 22, undesirably increasing the risk of breakage of the tether 22 during the procedure. It is therefore important that due care is taken to keep the distal tip 74 of the intermediary catheter 56 inside the vessel 68 during performance of the method of the present invention.

As mentioned above, there are several useful variations of the method of the present invention. For example, there may be circumstances under which the nature of the vessel 68 or the catheter allows the retrograde-antegrade guide wire 12 to be introduced into the catheter directly, without the need for the inserter sheath 60. This may occur when the vessel 68 is not a blood vessel and does not contain a continuous flow of fluid, so that bleeding or leakage between the catheter and the guide wire 12 is not of particular concern.

Such an arrangement is shown in FIG. 4, comparable to FIG. 3C, but lacking the inserter sheath 60. The retrograde-antegrade guide wire 12 is folded over on itself, and the pusher 86 moved in the direction of arrow 102 until it engages the curved end 16 of the elongated member 14, and advances the guide wire 12 into the lumen 58 of the intermediary catheter 56. The other steps in this method are the same as disclosed above.

As indicated before, the catheter employed with the retrograde-antegrade guide wire 12 need not be the intermediary catheter 56, but can instead be a conventional, operable catheter. Such a catheter could be directly substituted in the method disclosed with respect to the intermediary catheter 56; the resulting method need not be repeated here.

Other variations on the apparatus and method of the present invention should be clear to those skilled in this art. For example, the retrograde-antegrade reversal achieved by the guide wire 12 of the present invention could be obtained with a conventional guide wire, employed with a catheter or catheter segment having a flexible but curved distal tip. The conventional guide wire, initially extending in a first direction, would be proximally withdrawn past the curved distal tip, and the catheter proximally withdrawn until only the curved distal tip remained in the vessel or other tubular structure. The catheter would then be rotated to point the curved distal tip in the second direction, and the guide wire reinserted to allow complete advancement of the catheter or catheter segment in the second direction.

There may be some minor drawbacks to the use of the apparatus and method of the present invention. However, these drawbacks are generally greatly outweighed by the advantages of the present invention, and are generally subject to ready correction. The most significant concern would be the possibility of breakage of the tether 22 at the point where it flexes most sharply, that is, at the tip 20 of the curved end 16 of the elongated member 14. This concern is obviated by the preferred use of a multistrand tether 22, rather than a single wire tether. A second concern would be an inability to longitudinally withdraw the tip 20 of the elongated member 14 back into the distal tip 74 or 78 of the catheter 56 or 52, perhaps because the second end 18 of the elongated member 14 could not move past the tip 74 or 78, or because the member 14 somehow becomes hung up on some structure in the vessel or other tubular structure 68. This second concern is obviated by the fact that the second end 18 of the elongated member 14 is bent only a modest amount. However, if either of these concerns becomes problematic in any particular patient, they can be managed by the insertion of a snare from the contralateral side, to grasp and remove the member 14. A final concern would be an inability to reverse the direction of the catheter 56 or 52 because the angle of the initial puncture establishing the access site 66 was too acute. This concern is obviated by careful attention to the preparation of the access site. If this concern becomes problematic, a second access site can of course be prepared having a larger angle of entry.

Despite these minor drawbacks, it should be clear that the present invention admirably provides a catheterization apparatus which is advantageous in that it permits the reversal of the direction of catheterization while avoiding the need to establish a second access site. The catheterization apparatus of the present invention is relatively simple and yet reliable in construction and use, and is relatively low in cost, at least in comparison to the costs and risks incurred in establishing a second access site. The apparatus is atraumatic during use, that is, it does not significantly damage the blood vessel or other vessel during reversal of the direction of catheterization. The apparatus is useful in vessels of both large and small diameter. Indeed, the apparatus and method of the present invention are particularly effective when employed in the catheterization of vessels and other tubular structures of smaller diameter. For example, it is expected that the manufacture of smaller gauge guide wire segments than those specifically disclosed herein will allow the present invention to be used to reverse the direction of 4 French or even smaller diameter catheters in the vessels and other tubular structures in pediatric patients. Finally, the present invention facilitates the selective engagement of a catheter with a bifurcation branch in a vessel.

Any undisclosed or incidental details of the construction or composition of the various elements of the disclosed embodiment of the present invention are not believed to be critical to the achievement of the advantages of the present invention, so long as the elements possess the characteristics needed for them to perform as disclosed. The selection of these and other details of construction are believed to be well within the ability of one of even rudimentary skills in this area, in view of the present disclosure.

Industrial Applicability

The present invention is useful in performing surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A catheterization apparatus (10) comprising a retrograde-antegrade guide wire (12) foldable upon itself for partial introduction into a vessel (68) in a patient, the guide wire (12) comprising:

a resilient, elongated member (14) entirely receivable in the vessel (68) and having a flexible, curved end (16) and a remainder (17), the curved end (16) of the elongated member (14) having a tip (20); and a flexible tether (22) external to the elongated member (14) and connected to the tip (20) of the curved end (16) of the elongated member (14).

2. The apparatus (10) according to claim 1, wherein the curved end (16) of the elongated member (14) is more flexible than the remainder (17) of the elongated member (14).

3. The apparatus (10) according to claim 1, wherein the elongated member (14) includes a wire core (24).

4. The apparatus (10) according to claim 3, wherein the wire core (24) has first (26) and second (28) tapered ends.

5. The apparatus (10) according to claim 1, wherein the elongated member (14) includes a continuous coiled wire (30).

6. The apparatus (10) according to claim 5, wherein the elongated member (14) further comprises a wire core (24) over which the coiled wire (30) is positioned.

7. The apparatus (10) according to claim 6, wherein the wire core (24) has first (26) and second (28) tapered ends.

8. The apparatus (10) according to claim 7, wherein the tether (22) is affixed to the first end (26) of the wire core (24) of the elongated member (14).

9. The apparatus (10) according to claim 6, wherein the wire core (24) includes first (26) and second (28) ends; wherein the coiled wire (30) includes a portion (36) extending beyond the second end (28) of the wire core (24); and wherein the guide wire (12) further comprises a safety wire (38) connecting the second end (28) of the wire core (24) and the extending coiled wire portion (36).

10. The apparatus (10) according to claim 5, wherein the continuous coiled wire (30) includes a first end (32) adjacent to the tether (22); and wherein the guide wire (12) further comprises a short coiled wire segment (46) attached to the first end (32) of the continuous coiled wire (30), connecting the tether (22) and the coiled wire (30).

11. The apparatus (10) according to claim 1, wherein the remainder (17) of the elongated member (14) includes an atraumatic tip (44) opposite the curved end (16).

12. The apparatus (10) according to claim 1, wherein the remainder (17) of the elongated member (14) includes a second end (18) opposite the curved end (16), bent at an angle of about 10 to 15 degrees.

13. The apparatus (10) according to claim 1, further comprising a highly flexible catheter (56) having a lumen (58) dimensioned to allow passage of the guide wire (12) therethrough when the guide wire (12) is folded upon itself.

14. The apparatus (10) according to claim 13, further comprising an inserter sheath (60) engageable with the catheter (56) and having a lumen (62) dimensioned to receive the elongated member (14) of the guide wire (12) therein.

15. A catheterization apparatus (10) comprising a retrograde-antegrade guide wire (12) foldable upon itself for partial introduction into a vessel (68) in a patient, the guide wire (12) comprising:

resilient, elongated member (14) having a flexible, curved end (16) and a remainder (17), the curved end (16) having a tip (20), and the curved end (16) being more flexible than the remainder (17) of the elongated member (14); and a flexible tether (22) connected to the tip (20) of the curved end (16) of the elongated member (14);

wherein the remainder (17) of the elongated member (14) includes a second end (18) opposite the curved end (16), bent at an angle of about 10 to 15 degrees;

wherein the elongated member (14) comprises a wire core (24) having first (26) and second (28) tapered ends, and a continuous coiled wire (30) positioned over the wire core (24);

wherein the coiled wire (30) includes a portion (36) extending beyond the second end (28) of the wire core (24) of the elongated member (14), and the guide wire (12) further comprises a safety wire (38) connecting the second end (28) of the wire core (24) and the coiled wire portion (36); and wherein the continuous coiled wire (30) has a first end (32) adjacent to the tether (22), and the guide wire (12) further comprises a short coiled wire segment (46) attached to the first end (32) of the continuous coiled wire (30), connecting the tether (22) and the coiled wire (30).

* * * * *